US008647344B2

(12) United States Patent
Suzuki et al.

(10) Patent No.: US 8,647,344 B2
(45) Date of Patent: Feb. 11, 2014

(54) TREATMENT INSTRUMENT FOR ENDOSCOPE

(75) Inventors: Keita Suzuki, Tokyo (JP); Megumi Kimura, Tokyo (JP)

(73) Assignee: Olympus Medical Systems Corp., Tokyo (JP)

(*) Notice: Subject to any disclaimer, the term of this patent is extended or adjusted under 35 U.S.C. 154(b) by 18 days.

(21) Appl. No.: 13/309,672

(22) Filed: Dec. 2, 2011

(65) Prior Publication Data

US 2012/0078040 A1    Mar. 29, 2012

Related U.S. Application Data

(63) Continuation of application No. PCT/JP2010/062522, filed on Jul. 26, 2010.

(30) Foreign Application Priority Data

Sep. 15, 2009   (JP) ................. P2009-212944

(51) Int. Cl.
   *A61B 18/18*   (2006.01)
(52) U.S. Cl.
   USPC ............................. 606/51; 606/46
(58) Field of Classification Search
   USPC .............. 606/41, 46, 51, 52; 600/104, 134
   See application file for complete search history.

(56) References Cited

U.S. PATENT DOCUMENTS 6,102,909 A *   8/2000   Chen et al. ............... 606/45
6,273,887 B1 *  8/2001   Yamauchi et al. ........ 606/48

2003/0229344 A1   12/2003   Dycus et al.
2004/0249411 A1 *  12/2004   Suzuki ................. 606/205
2005/0033358 A1 *  2/2005    Suzuki ................. 606/207
2005/0187547 A1 *  8/2005    Sugi .................... 606/48
2008/0294159 A1 *  11/2008   Akahoshi et al. ...... 606/41

(Continued)

FOREIGN PATENT DOCUMENTS

EP    1743589 A2    1/2007
JP    S58-83950     5/1983

(Continued)

OTHER PUBLICATIONS

English-language Abstract of Japanese Patent Publication No. 2004-321660, dated Nov. 18, 2004.

(Continued)

*Primary Examiner* — Linda Dvorak
*Assistant Examiner* — Jocelyn D Ram
(74) *Attorney, Agent, or Firm* — Scully, Scott, Murphy & Presser, P.C.

(57) ABSTRACT

A treatment instrument for endoscope includes a first and a second forceps members having a conductive electrode part; a forceps rotation axis that supports the forceps members so that they can rotate relative to each other, a first and a second link members being connected via a rotation axis to the forceps members respectively, and make the forceps members open and close, a link support member supporting the forceps members in a state where they are separated at a predetermined interval when they are opened and closed, an operation part connecting to the link support member, and opens and closes the forceps members by moving the link members, and a power supply wire, one end thereof being connected to the electrode part by being attached to the forceps rotation axis, and another end thereof being connected to a current supply means providing a current to the electrode part.

5 Claims, 14 Drawing Sheets

(56) References Cited

U.S. PATENT DOCUMENTS

| | | | |
|---|---|---|---|
| 2011/0098703 A1* | 4/2011 | Suzuki et al. | 606/41 |
| 2011/0137115 A1* | 6/2011 | Suzuki | 600/104 |
| 2012/0029507 A1* | 2/2012 | Kimura et al. | 606/41 |
| 2012/0136424 A1* | 5/2012 | Kimura et al. | 607/154 |

FOREIGN PATENT DOCUMENTS

| | | |
|---|---|---|
| JP | 2005-034623 | 2/2005 |
| JP | 2006-518258 | 8/2006 |
| JP | 2007-289593 | 11/2007 |
| JP | 2008-000582 A | 1/2008 |
| JP | 2008-005965 | 1/2008 |
| JP | 2008-212620 | 9/2008 |
| JP | 4197983 | 10/2008 |

OTHER PUBLICATIONS

International Search Report dated Oct. 5, 2010 issued in PCT/JP2010/062522.

European Search Report dated Aug. 2, 2013 issued in European Patent Application No. 10816973.1.

* cited by examiner

TREATMENT INSTRUMENT FOR ENDOSCOPE

This application is a continuation application based on a PCT Patent Application No. PCT/JP2010/062522, filed Jul. 26, 2010, whose priority is claimed on Japanese Patent Application No. 2009-212944, filed in Japan on Sep. 15, 2009. The contents of both the PCT Application and the Japanese Application are incorporated herein by reference.

BACKGROUND OF THE INVENTION

1. Technical Field

The present invention relates to a treatment instrument for endoscope, and more specifically relates to a treatment instrument for endoscope that is endoscopically inserted into a body cavity.

2. Description of Related Art

There is a conventionally known treatment instrument for endoscope that is endoscopically inserted into a body cavity and used in carrying out various types of treatment to a body cavity tissue of a patient or the like (hereinafter termed as 'treatment instrument').

As one example of a treatment instrument, Japanese Patent No. 4197983 describes a forceps. A pair of forceps members are provided at a distal end of the forceps, and are supported via a rotation axis so as to be able to rotate relative to each other.

The pair of forceps members are connected by operation wires to an operation part on the holding side. Two link members are attached at the distal ends of the operation wires so as to be able to rotate. The distal ends of the link members are respectively attached to proximal ends of one and another of the pair of forceps members so as to be able to rotate.

With this configuration, by advancing and retracting the operation wire in the axial direction via the operation part, the pair of forceps members can be rotated relative to each other around the rotation axis and thereby opened and closed.

SUMMARY OF THE INVENTION

According to a first aspect of the present invention, a treatment instrument for endoscope includes a first forceps member and a second forceps member having a conductive electrode part, a forceps rotation axis that supports the first forceps member and the second forceps member so as to be capable of rotating relative to each other; a first link member and a second link member being connected via a rotation axis to the first forceps member and the second forceps member respectively, and make the first forceps member and the second forceps member open and close, a link support member supporting the first forceps member and the second forceps member in a state where the first forceps member and the second forceps member are separated at a predetermined interval when the first forceps member and the second forceps member are opened and closed, an operation part connecting to the link support member, the operation part opening and closing the first forceps member and the second forceps member by moving the first link member and the second link member, and a power supply wire, one end thereof being connected to the electrode part by being attached to the forceps rotation axis, and another end thereof being connected to a current supply means providing a current to the electrode part, the power supply wire being disposed in a separated section formed between the first link member and the second link member at a predetermined interval by the link support member. A displacement of a connection part of the first forceps member or the second forceps member corresponding to at least one of the first link member and the second link member toward the separated section is restricted by the power supply wire.

According to a second aspect of the present invention, the treatment instrument for endoscope further includes an operation member being provided with the link support member attached on a distal end thereof, the operation member being connected with the operation part, a coil sheath which the operation member is inserted into, and a tube sheath which the coil sheath is inserted into, and which is capable of rotating around an axis relative to the coil sheath. The relative movement of the coil sheath in the axial direction of the tube sheath is restricted by an advance/retraction restriction member attached in a lumen that is separated by more than a predetermined length from a distal end of the tube sheath. The coil sheath and the tube sheath maintain flexibility between the advance/retraction restriction member and the connection member.

Preferably, the power supply wire is disposed parallel to the operation member over a range from the one end to the another end.

Preferably, the first link member and the second link member are parallel in the state where the first forceps member and the second forceps member are closed.

According to the third aspect of the present invention, the electrode part of the first forceps member and the electrode part of the second forceps member are insulated from each other. The two power supply wires are provided, one end of each of the power supply wires is connected with the electrode part of the first forceps member and the electrode part of the second forceps member, respectively. Displacements of connection parts between the first link member and the second link member and the first forceps member and the second forceps member toward the separated section are restricted.

DETAILED DESCRIPTION OF THE INVENTION

Figure 1:
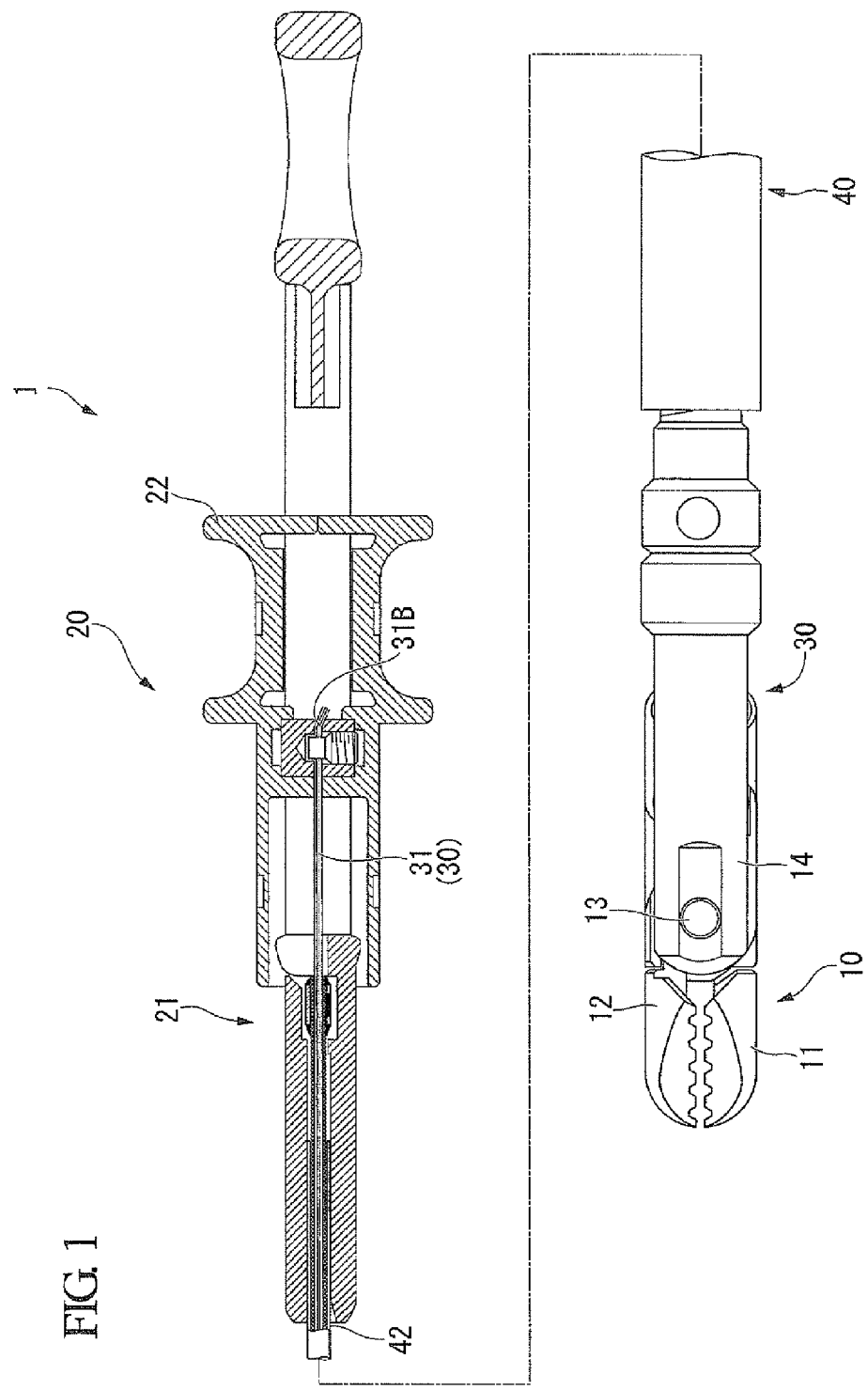
FIG. 1 is a diagram of an entire treatment instrument for endoscope according to a first embodiment of the present invention.

A treatment instrument for endoscope according to a first embodiment of the present invention will be explained with reference to FIGS. 1 to 6. A treatment instrument 1, which is a treatment instrument for endoscope of this embodiment, includes a treatment part 10 for carrying out treatment to a body cavity tissue, an operation part 20 for operating the treatment part 10, a connection part 30 for connecting the treatment part 10 to the operation part 20, and an elongated insertion part 40 that is inserted into a body cavity.

The treatment part 10 is constituted by a pair of forceps including a first forceps member 11 and a second forceps member 12, which are supported by a forceps rotation axis 13 so as to be able to rotate relative to each other. The forceps rotation axis 13 is supported by a cover 14 disposed such as to sandwich the first forceps member 11 and the second forceps member 12.

The operation part 20 includes a main part 21 which the insertion part 40 is attached to, and a slider 22 attached to the main part 21 so as to be able to slide.

The slider 22 and the treatment part 10 are connected by the connection part 30, and the pair of forceps members 11 and 12 can be opened and closed by sliding the slider 22 in a longitudinal direction of the main part 21. This point will be described in greater detail when an operation performed during use is explained below.

Figure 2:
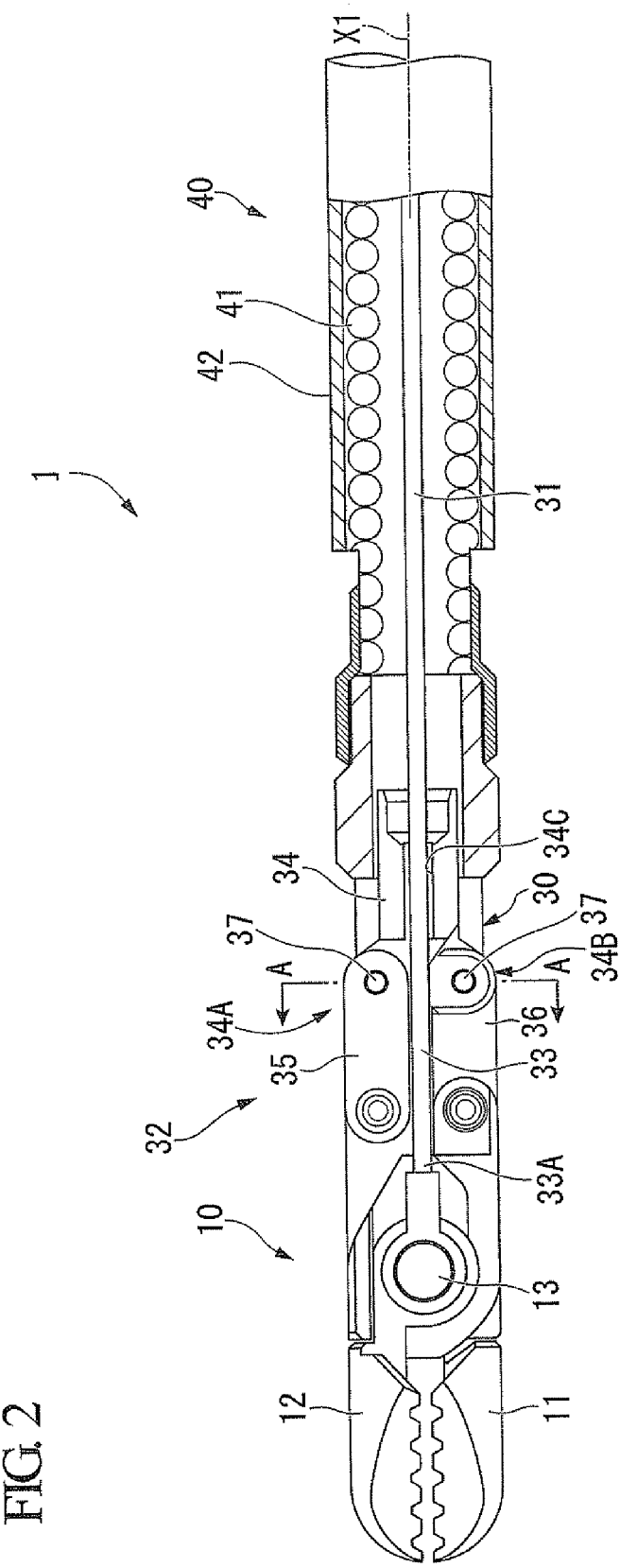
FIG. 2 is a diagram of the vicinity of a treatment part of the treatment instrument for endoscope with its cover removed according to the first embodiment of the present invention.
Figure 3:
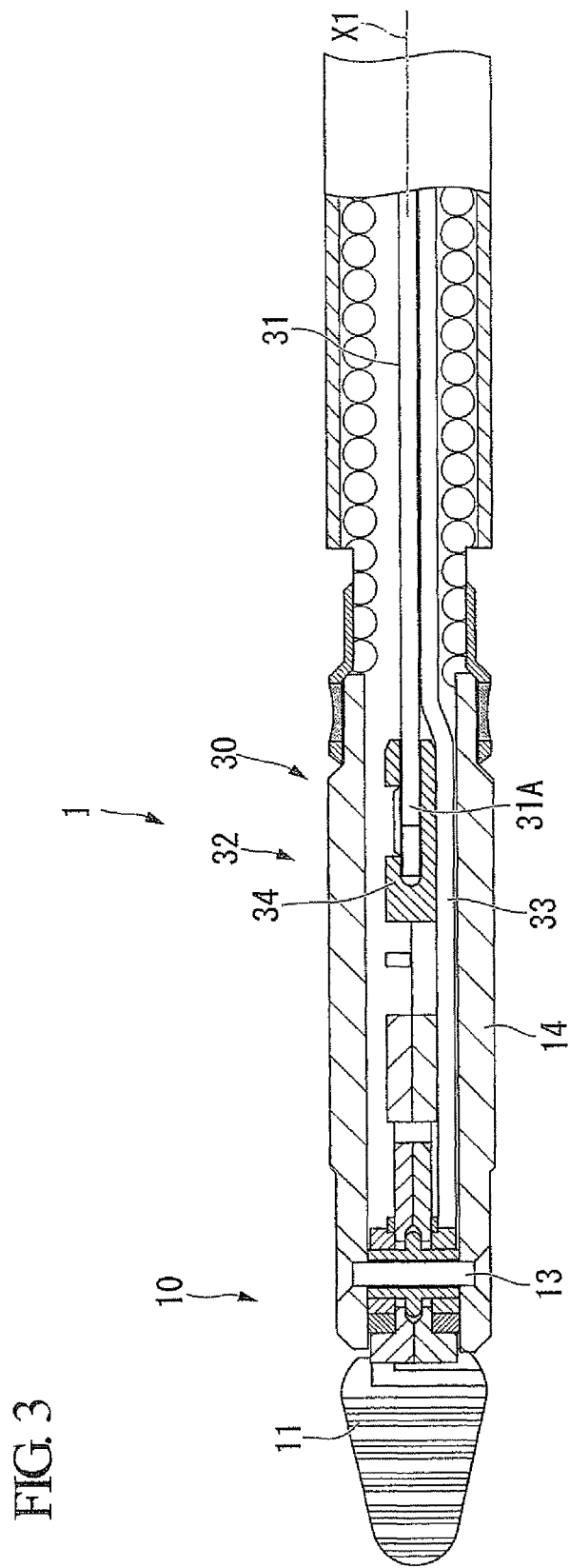
FIG. 3 is a cross-sectional diagram of the vicinity of a treatment part according to the first embodiment of the invention.

FIG. 2 is a diagram of the vicinity of the treatment part 10 of the treatment instrument 1 with the cover 14 removed, and FIG. 3 is a cross-sectional diagram of the vicinity of the treatment part 10 viewed from another angle. As shown in FIGS. 2 and 3, the connection part 30 includes an operation wire 31, a link mechanism 32 attached to a distal end of the operation wire 31, and a restriction wire (restriction part) 33 for guiding the advance/retraction of the link mechanism 32. The operation wire 31 has a heretofore known configuration, a first end part 31A on the distal-end side being connected to the link mechanism 32, and a second end part 31B on the proximal-end side (see FIG. 1) being connected to the slider 22 of the operation part 20.

The link mechanism 32 includes a connection member 34 attached to the distal end of the operation wire 31, and a pair of link members, namely a first link member 35 and a second link member 36, which connect the connection member 34 to the pair of forceps members 11 and 12.

The connection member 34 includes two link rotation axes 34A and 34B on its distal-end side. Pins 37 connect the proximal ends of the first link member 35 and the second link member 36 respectively to the link rotation axes 34A and 34B so that they are able to rotate. A groove 34C is formed in the connection member 34 and extends parallel to the axis X1 of the operation wire 31.

The link rotation axes 34A and 34B are set at equal distances (including approximate distances) away from the axis X1 of the operation wire, and face each other with the axis X1 between them. The axes of the two pins 37 are parallel (including substantially parallel), and the two link rotation axes 34A and 34B are arranged parallel to each other.

The distal-end sides of the first link member 35 and the second link member 36 are linked respectively to the proximal-end sides of the first forceps member 11 and the second forceps member 12 so as to be able to rotate. When the pair of forceps (first forceps member 11 and second forceps member 12) are in the closed state, the first link member 35 and the second link member 36 are parallel to each other.

A first end part 33A of the restriction wire 33 is connected to the forceps rotation axis 13, and a second end part (not shown) is connected through the insertion part 40 to the main part 21 of the operation part 20. The restriction wire 33 is disposed parallel (including substantially parallel) to the axis X1 of the operation wire 31 so as to run inside the groove 34C of the connection member 34.

Figure 4:
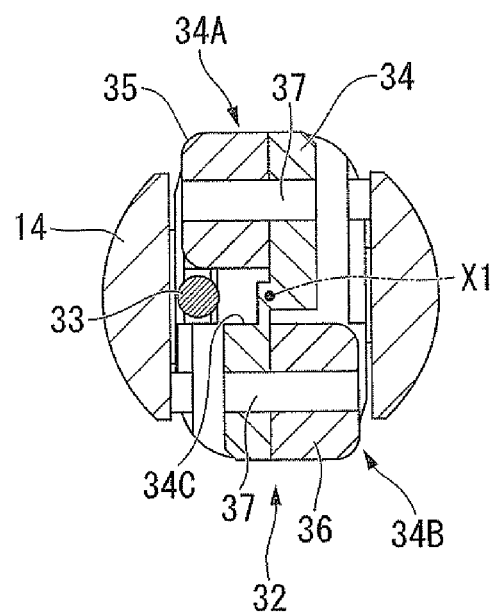
FIG. 4 is a cross-sectional view along the line A-A in FIG. 2.

FIG. 4 is a cross-sectional view along the line A-A of FIG. 2. As shown in FIG. 4, a face of the connection member 34 that is orthogonal to the axis X1 is shaped like a crank in cross-section, so that the point where the link rotation axis 34A is formed and the point where the link rotation axis 34B is formed are mutually different with the axis X1 between them. This ensures that the maximum thickness of the link mechanism 32 on each of the link rotation axes 34A and 34B is a value approximately near the sum of the thickness of the connection member 34 and the thicknesses of the link members 35 and 36 respectively, and is thus suppressed to the thickness of two members.

Figure 5:
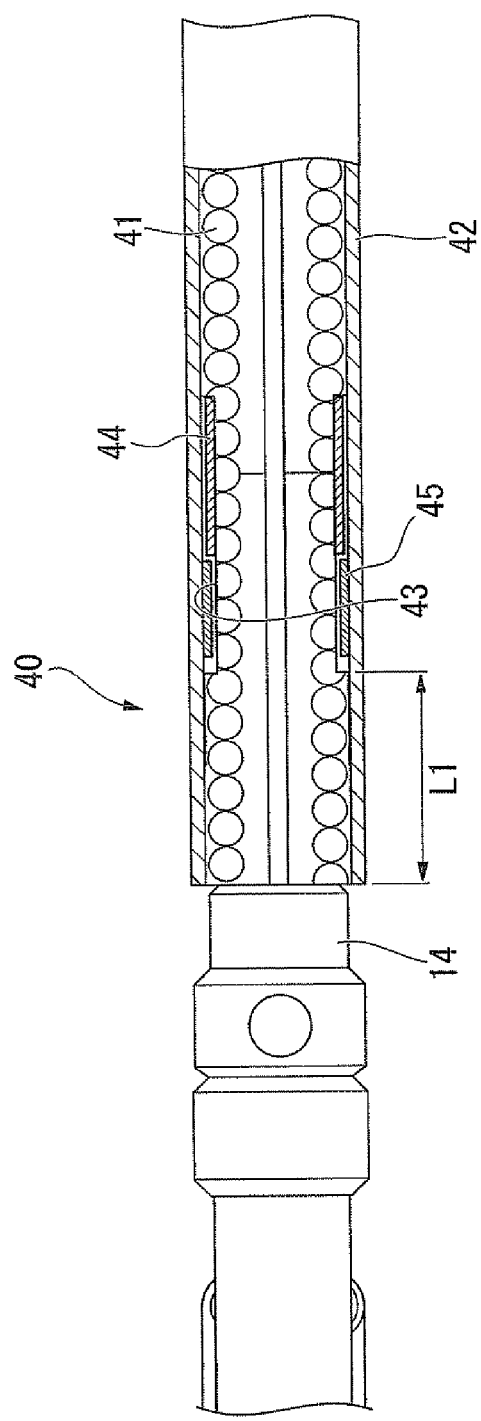
FIG. 5 is a cross-sectional diagram of one part of an insertion part of the treatment instrument for endoscope according to the first embodiment of the present invention.

FIG. 5 is a cross-sectional diagram of one part of the insertion part 40. The insertion part 40 includes a coil sheath 41 which the operation wire 31 is inserted into, and a tube sheath 42 which the coil sheath 41 is inserted into.

The coil sheath 41 can be selected as appropriate from any heretofore known type of coil sheath. The cover 14 is attached to the distal end of the coil sheath 41. The proximal end of the coil sheath 41 is secured to the main part 21 of the operation part 20.

As shown in FIG. 5, a small-diameter part 43 whereof an outer peripheral face has been cut away to reduce the outer diameter, is formed on the coil sheath 41 at a point on the proximal-end side at a predetermined length L1 from the distal end. The coil sheath 41 is divided into two parts in this small-diameter part 43, and is made into a single coil sheath by soldering or the like via a connection ring 44 attached to the small-diameter part 43.

The tube sheath 42 can also be selected as appropriate from any type of heretofore known tube sheath formed from resin and the like. While the proximal end of the tube sheath 42 is inserted into the opening provided in the distal end of the main part 21, it can rotate relative to the main part 21. A ring member (advance/retraction restriction member) 45, which is fitted into the small-diameter part 43 of the coil sheath 41, is pressed into the tube sheath 42. When the ring member 45 is in the pressed-in state, its inner diameter is smaller than the basic outer diameter of the coil sheath 41 (the diameter of points other than the small-diameter part 43) and the outer diameter of the connection ring 44. The inner diameter of the ring member 45 is larger than the outer diameter of the small-diameter part 43, ensuring that there is clearance between them.

With this configuration, the coil sheath 41 and the tube sheath 42 are able to rotate relative to each other around the axis, yet are actually unable to move relative to each other in the axis direction. To realize a configuration such as the one described above, one coil sheath with a small-diameter part 43 is divided into two at its small-diameter part 43. In a state where the ring member 45 fitted into the small-diameter part of the distal-end side coil sheath, the pieces of coil sheath cut away are connected in one piece using the connection ring 44. The coil sheath 41 with the ring member 45 attached thereto is then inserted into the tube sheath 42, and the ring member 45 is pressed into the tube sheath 42, completing the insertion part 40 of the treatment instrument 1.

Although the predetermined length L1 can be set as appropriate, the insertion part 40 between the connection member 34 of the connection part 30 and the ring member 45 is preferably set to a length that enables it to deform sufficiently, e.g. 20 millimeters (mm), so as to shorten its actual hard length (explained below) on the distal-end side of the treatment instrument 1.

An operation performed when using the treatment instrument 1 with the above configuration will be explained.

Firstly, an endoscope (not shown) is inserted into the body of a patient, and the distal end of the endoscope is advanced to the vicinity of a body cavity tissue (target tissue) that is the target of the treatment.

The slider 22 is then retracted with respect to the main part 21 of the operation part 20 so as to close the pair of forceps (first forceps member 11 and second forceps member 12), and the insertion part 40 is inserted into the forceps channel of the endoscope. The treatment part 10 is then protruded from the distal end of the forceps channel. At this time, the section of the connection part 30 that is covered by the cover 14 and the treatment part 10 on the distal end of the treatment instrument 1 is separated from the point on the insertion part 40 where the ring member 45 is provided by the predetermined length L1. This maintains the flexibility of the insertion part 40 between them. As a result, even if the endoscope meanders and the like inside the body cavity, it can bend and deform well so as to follow the meandering shape, enabling the treatment instrument 1 to be favorably inserted into the forceps channel of the endoscope.

Figure 6:
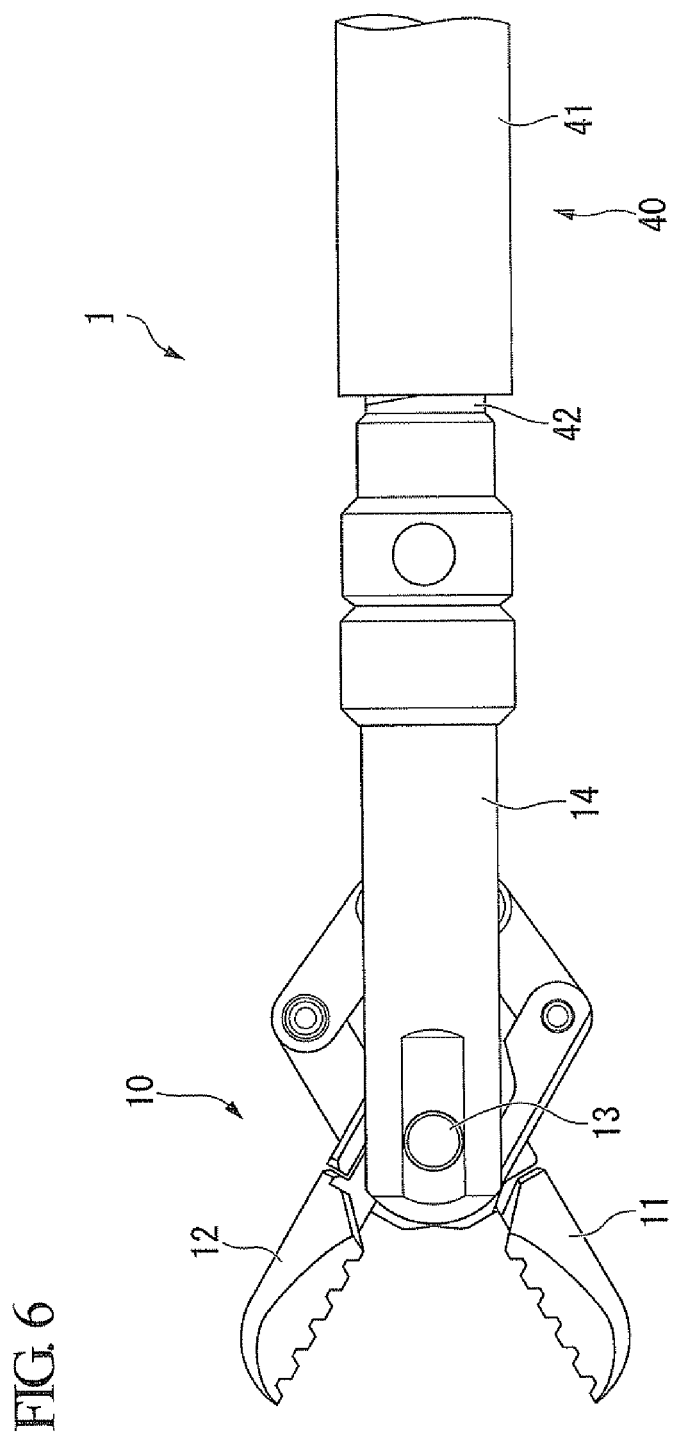
FIG. 6 is a diagram of an operation performed when using the treatment instrument for endoscope according to the first embodiment of the present invention.

In performing treatment, the slider 22 is moved forward with respect to the main part 21. The operation wire 31 connected to the slider 22 moves forward with respect to the coil sheath 41. Since the forceps rotation axis 13 is supported by the cover 14 attached to the coil sheath 41 as described above, the first forceps member 11 and the second forceps member 12 each rotate around the forceps rotation axis 13, and the treatment part 10 opens as shown in FIG. 6.

At this time, the operation wire 31 and the connection member 34 attached to its distal end advance and retract along the restriction wire 33 arranged parallel to the axis X1 of the operation wire 31 due to the engagement between the groove 34C and the restriction wire 33. Therefore, the operation wire 31 and the connection member 34 can be advanced and retracted while restricting them from moving in a direction relative to the forceps rotation axis 13, and while preventing the connection member 34 from escaping in the direction leading away from the axis X1. As a result, the pair of forceps members (first forceps member 11 and second forceps member 12) can be opened and closed well.

While opening and closing the pair of forceps members (first forceps member 11 and second forceps member 12) of the treatment part 10 by advancing and retracting the slider 22, the user treats the target tissue. If necessary, he can adjust the positional relationship of the open/close faces of the pair of forceps members (first forceps member 11 and second forceps member 12) and the target tissue, by rotating the main part 21 around the axis to rotate the treatment part 10.

According to the treatment instrument 1 of the present embodiment, the connection member 34 is provided with the two link rotation axes 34A and 34B which are set apart from each other in the axis X1 of the operation wire 31, and which the first link member 35 and the second link member 36 are respectively connected to. Therefore, the thicknesses of the connection points between connection member 34 and the link members 35 and 36 in the axis direction of the respective link rotation axes 34A and 34B have the thickness of two members, being the sum thickness of the connection member 34 and one of the link members (first link member 35 and second link member 36) along their entire length. As a result, in comparison with a conventional structure where two link members are connected on a single rotation axis, the distal-end side region including the treatment part can be made even thinner.

Furthermore, one part of the connection part 30 and the hard treatment part 10 provided at the distal end of the treatment instrument 1, and the ring member 45 that connects the coil sheath 41 to the tube sheath 42 so that they can rotate relative to each other in the insertion part 40, are set apart by a predetermined length L1. Therefore, when the ring member 45 and the hard treatment part 10 and the like are near to each other, it is possible to actually shorten the hard length of the distal-end side of the treatment instrument 1, being the sum of their lengths in the axial direction. The treatment instrument consequently has good insertability into the endoscope.

In many conventional treatment instruments, a structure for connecting the coil sheath 41 and the tube sheath 42 so that they can rotate relative to each other is provided near the distal end of the tube sheath. This leads to problems in that it increases the hard length of the treatment instrument distal end, makes it difficult to insert and retract the treatment instrument into/from a forceps channel, requires a large amount of force to the endoscope, and so on. The structure of the insertion part 40 of the treatment instrument 1 of this embodiment solves these problems.

Subsequently, a second embodiment of the present invention will be explained with reference to FIGS. 7 to 9. A difference between a treatment instrument 51 of this embodiment and the treatment instrument 1 of the first embodiment is that electrical power is conducted to the treatment part through the restriction wire.

In the following explanation, constitutive elements which are common to the treatment instruments of each embodiment are designated with like reference numerals and are not repetitiously explained.

Figure 7:
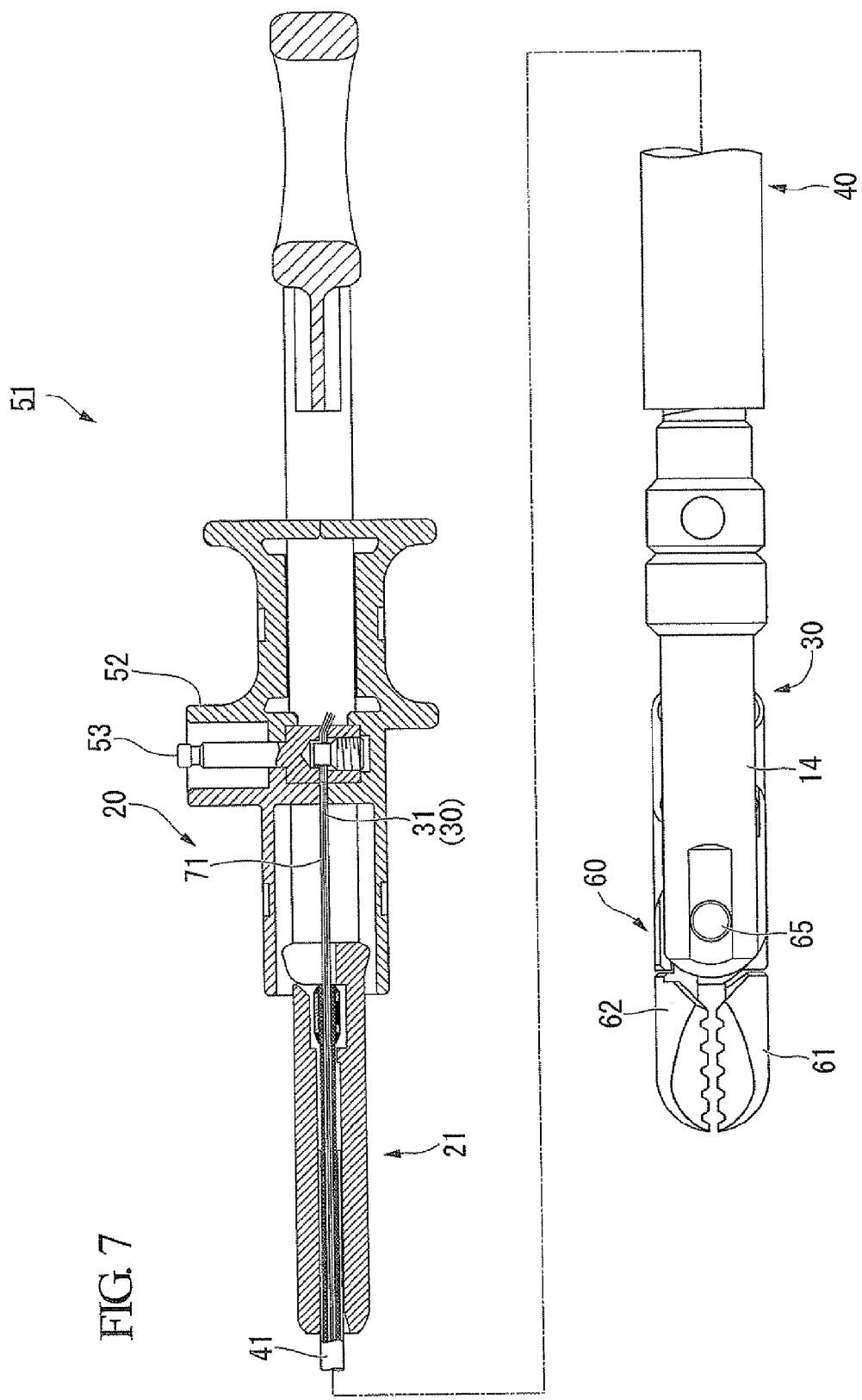
FIG. 7 is an overall diagram of a treatment instrument for endoscope according to a second embodiment of the present invention.

FIG. 7 is an overall diagram of a treatment instrument 51. The operation part 20 is provided with a slider 52 instead of the slider 22, and the slider 52 includes a plug 53 which connects to a high-frequency power source (not shown).

Figure 8:
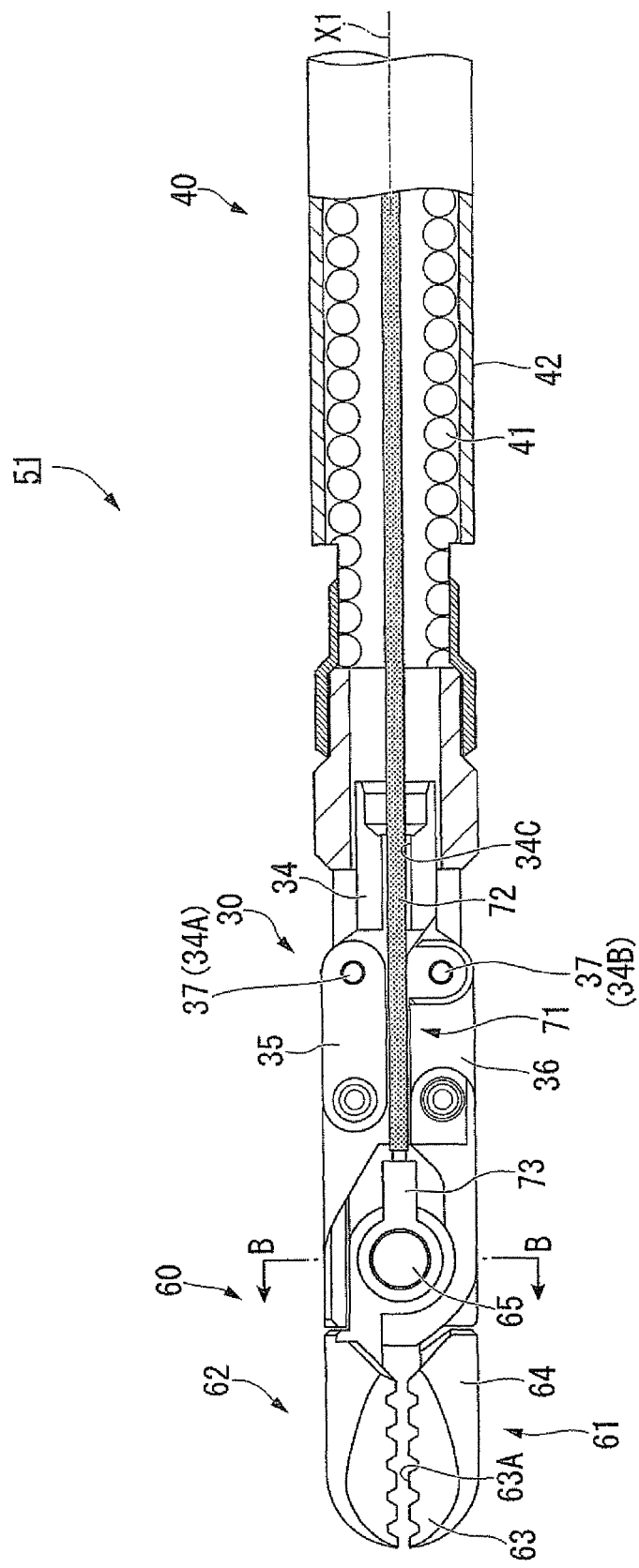
FIG. 8 is a diagram of the vicinity of a treatment part of the treatment instrument for endoscope with its cover removed according to the second embodiment of the present invention.

FIG. 8 is a diagram of the vicinity of a treatment part 60 of the treatment instrument 51 with the cover 14 removed. The treatment part 60 includes a first forceps member 61 and a second forceps member 62, instead of the pair of forceps members 11 and 12.

The second forceps member 62 on the upper side of FIG. 8 is formed from a ceramic member such as alumina or zirconia, or a resin such as polytetrafluoroethylene (PTFE) or polyether ether ketone (PEEK: Registered Trademark), and has insulating properties.

Instead of this configuration, the second forceps member 62 can be formed by coating the entire top face of a core made from a metal such as stainless steel with the insulating member described above or an insulation coating.

The first forceps member 61 on the lower side of FIG. 8 includes an electrode part 63 where an electrode face 63A formed from a conductor such as stainless steel is exposed, and an insulation part 64 provided such as to cover a part of the electrode part 63. The electrode face 63A is preferably provided on an opening and closing face where the pair of forceps members (first forceps member 61 and second forceps member 62) face each other and make contact with the body cavity tissues at least during treatment. The area of the electrode face 63A is preferably smaller to facilitate the concentration of energy.

The insulation part 64 can be formed by using a member with insulating properties similar to those of the second forceps member 62 to cover a part of the top face of the electrode part 63, or by applying an insulation coating. In order to ensure that current supplied to the electrode part 63 does not leak to metal parts such as the treatment part 60 and the connection part 30, the insulation part 64 is provided so as to cover all the parts that are likely to make contact with, for example, the link members 35 and 36 and the cover 14. Therefore, the top faces of parts of the first forceps member 61 that are further to the proximal-end side than a forceps rotation axis 65 (explained below) are all covered with the insulation part.

Figure 9:
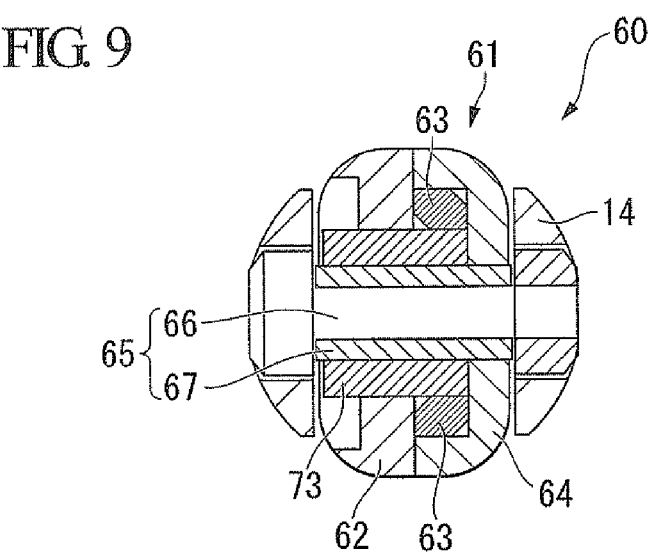
FIG. 9 is a cross-sectional view along the line B-B in FIG. 8.

FIG. 9 is a cross-sectional view along the line B-B in FIG. 8. As shown in FIG. 9, a forceps rotation axis 65 links the pair of forceps members (first forceps member 61 and second forceps member 62) so that they can rotate relative to each other. The forceps rotation axis 65 includes a core body 66 made from a conductor, and a cylindrical part (insulating layer) 67 for insulating and covering the outer peripheral face of the core body 66. The cylindrical part 67 may be formed from a member made of an insulating material, or from an insulating layer made of an insulation coating.

As shown in FIG. 8, the connection part 30 is provided with a restriction wire 71 instead of the restriction wire 33. The proximal-end side (second end) of the restriction wire 71 is electrically connected to the plug 53, and the restriction wire 71 also functions as a power supply wire for supplying a high-frequency current to the electrode part 63 of the treatment part 60. To ensure that the current does not leak to metal parts other than the electrode part 63, an insulating coat 72 is provided over almost the entire length of the restriction wire 71 except its ends.

A cylindrical rotation contact-point member 73 is attached to the distal end (first end) of the restriction wire 71. As shown in FIG. 9, the rotation contact-point member 73 is fitted to the outer side of the cylindrical part 67 so that it is coaxial with the forceps rotation axis 65. It is then electrically connected to one part of the electrode part 63 which is exposed so that it is facing the outer peripheral face of the cylindrical part 67.

In the structure described above, the distal end of the restriction wire 71 is attached to the forceps rotation axis 65 so that it can rotate freely, and the high-frequency current can be supplied only to the electrode part 63 of the first forceps member 61. Also, as shown in FIG. 8, when seen from the axial direction of the link rotation axes 34A and 34B, the restriction wire 71 is disposed between the first link member 35 and the second link member 36, the positional relationship being one where the restriction wire 71 does not overlap the link members 35 and 36.

With structures described above, the overall configuration of the treatment instrument 51 is that of a monopolar high-frequency treatment instrument.

An operation performed when using the treatment instrument 51 with the above configuration will be explained.

Firstly, an endoscope (not shown) is inserted into a patient's body which has been made to contact a heretofore known return electrode (not shown), and the distal end of the endoscope is advanced to the vicinity of a body cavity tissue that is the treatment target. The treatment part 60 is then protruded from the forceps channel by a procedure similar to that of the treatment instrument 1 in the first embodiment, and a high-frequency power source (not shown) and the plug 53 are connected by a power cable (not shown).

When the user positions the target tissue between the open pair of forceps members (first forceps member 61 and second forceps member 62) of the treatment part 60 and pulls the slider 52 in the direction away from the treatment part 60, the distal end of the pair of forceps members (first forceps member 61 and second forceps member 62) closes, whereby the target tissue is tucked down in the treatment part 60 and makes contact with the electrode face 63A.

If the user supplies a high-frequency current from the high-frequency power source in this state, the high-frequency current is supplied through the restriction wire 71 to the electrode part 63, cauterizing the target tissue on the electrode face 63A.

After completing the treatment has ended, the user removes the treatment instrument 51 from the forceps channel and removes the endoscope from the body of the patient, thereby ending the procedure.

According to the treatment instrument 51 of this embodiment, the restriction wire 71 is used as a power supply wire. Therefore, in comparison with a configuration where power is supplied via the operation wire 31, the link members 35 and 36 and the like need not be subjected to an insulating process or the like, making it possible to supply the high-frequency current more easily and more selectively to the electrode part 63.

The distal end of the restriction wire 71 is connected to the forceps rotation axis 65 by the rotation contact-point member 73 so that it can rotate. Therefore, no excessive force acts on the pair of forceps members (first forceps member 61 and second forceps member 62) when they open and close, favorably enhancing the opening/closing operation.

Moreover, since the rotation contact-point member 73 does not move in association with the opening and closing of the pair of forceps members (first forceps member 61 and second forceps member 62), it is not exposed outside the cover 14 during treatment. This favorably prevents the restriction wire 71 from unwanted contacting with body cavity tissue, and resultant current leakage.

Moreover, the rotation contact-point member 73 is attached by fitting it from the outside to the cylindrical part 67 of the forceps rotation axis 65 so that it is disposed between the cylindrical part 67 and the electrode part 63 exposed so as to face the outer peripheral face of the cylindrical part 67, and one part of the electrode part 63 is positioned on each side of the axis X1 of the rotation contact-point member 73. Therefore, when the slider 52 is retracted away from the treatment part 60 to close the pair of forceps members 61 and 62 during treatment, the restriction wire 71 is also retracted to the operation part 20 side. This operation also causes the rotation contact-point member 73 to be retracted to the operation part 20 side and pushed against a part of the electrode part 63, reliably achieving contact between the rotation contact-point member 73 and the electrode part 63, and enabling the high-frequency current to be conducted during treatment.

In addition, since the forceps rotation axis 65 includes the core body 66 made from a conductor such as metal, and the cylindrical part 67 that provides an insulating cover for the outer peripheral face of the core body 66, the forceps rotation axis 65 and the electrode part 63 can be kept insulated from each other, while easily achieving sufficient rigidity to withstand the force that acts on the forceps rotation axis 65 when the pair of forceps members (first forceps member 61 and second forceps member 62) is opened and closed.

Furthermore, since the restriction wire 71 functioning as a power supply wire and the pair of link members 35 and 36 are disposed such that they do not overlap when viewed from the axial direction of the link rotation axes 34A and 34B, the restriction wire 71 can be disposed linearly that runs between the parallel pair of link members 35 and 36 and is parallel to the axis X1 of the operation wire 31. As a result, the restriction wire 71 can favorably perform two functions: namely, guiding the sliding of the connection member 34 of the connection part 30, and supplying power to the electrode part 63.

Subsequently, a third embodiment of the present invention will be explained with reference to FIGS. 10 to 12. A difference between a treatment instrument 81 of the present embodiment and the treatment instruments of the embodiments described above is that the treatment instrument 81 is configured overall as a bipolar high-frequency treatment instrument.

Figure 10:
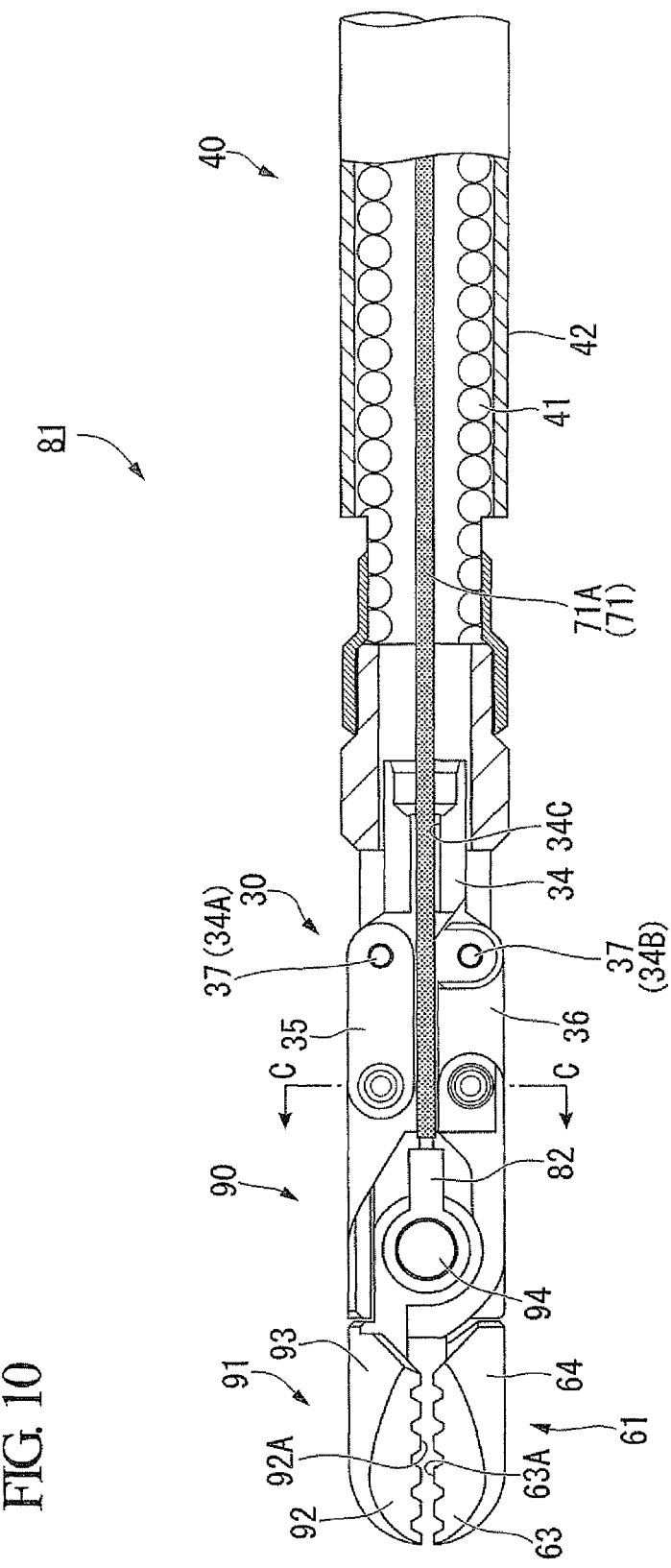
FIG. 10 is a diagram of the vicinity of a treatment part of the treatment instrument for endoscope with its cover removed according to a third embodiment of the present invention.
Figure 11:
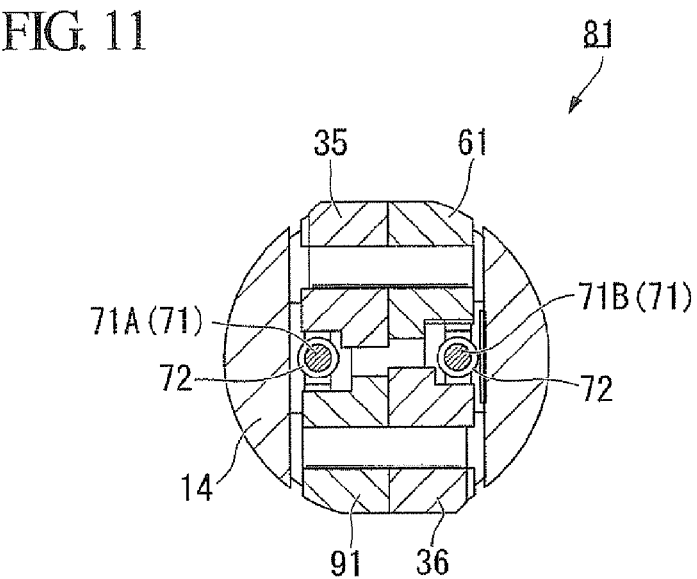
FIG. 11 is a cross-sectional view along the line C-C in FIG. 10.
Figure 12:
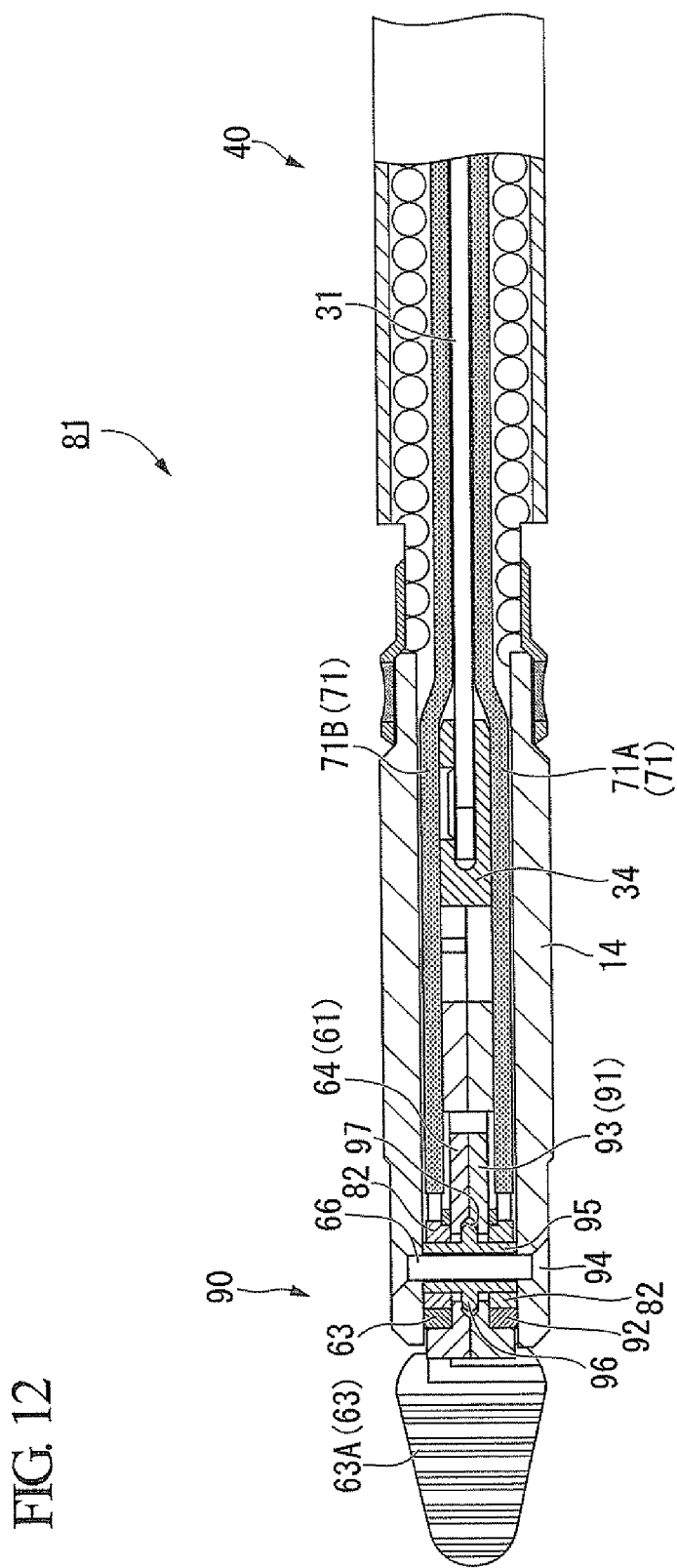
FIG. 12 is a cross-sectional diagram of the vicinity of a treatment part according to the third embodiment of the present invention.

FIG. 10 is a diagram of the vicinity of a treatment part 90 of the treatment instrument 81 with the cover 14 removed, and FIG. 11 is a cross-sectional view taken along the line C-C of FIG. 10. FIG. 12 is a cross-sectional view taken along a face parallel to a forceps rotation axis and an operation wire in the vicinity of the treatment part 90. As shown in FIGS. 10 to 12, in the treatment instrument 81, two restriction wires 71 functioning as power supply wires are connected to the treatment part 90. Accordingly, the connection member 34 has two grooves 34C, on one each face.

The treatment part 90 includes a pair of forceps members including a first forceps member 61 and a second forceps member 91. The second forceps member 91 has substantially the same structure as the first forceps member 61, including an electrode part 92 having an electrode face 92A, and an insulation part 93. The points where the first forceps member 61 and the second forceps member 91 make contact with each other are covered by the insulation parts 64 and 93 to prevent them from becoming conductive.

A forceps rotation axis 94 includes a core body 66 and a cylindrical part 95 with insulating properties. A flange (protrusion) 96 is provided around the entire circumference of the outer peripheral face of the cylindrical part 95, and protrudes radially outward. Notches are provided in parts of the mutually opposing faces of the first forceps member 61 and the second forceps member 91 which are connected to the forceps rotation axis 94, and the flange 96 penetrates a recess 97 formed by these notches.

While a rotation contact-point member 82 attached to the two restriction wires 71 is broadly the same shape as the rotation contact-point member 73 of the second embodiment, the cylindrical part attached by fitting from the outside to the forceps rotation axis 94 is shorter in the axial direction than the rotation contact-point member 73. As shown in FIGS. 10 and 12, one restriction wire 71A is electrically connected to the electrode part 92 of the second forceps member 91, while the other restriction wire 71B is electrically connected to the electrode part 63 of the first forceps member 61. The proximal ends of the restriction wires 71A and 71B are each connected to a high-frequency power source (not shown), forming high-frequency current circuits.

The method of using the treatment instrument 81 is similar to that of an ordinary bipolar high-frequency treatment instrument, and there is no need to install a return electrode. When the user tucks down a target tissue between the pair of forceps members 61 and 91 and conducts electrical power to the treatment part 90, a high-frequency current flows from the electrode face of one of the forceps members (e.g. electrode face 63A) toward the electrode face of the other forceps member (e.g. electrode face 92A), cauterizing the target tissue.

The treatment instrument 81 of this embodiment can obtain effects similar to those of the treatment instrument 1 of the first embodiment. Also, as in the treatment instrument 51 of the second embodiment, it enables the pair of forceps members to be opened and closed favorably while performing conductive treatment.

Moreover, the flange 96 is provided to the cylindrical part 95 of the forceps rotation axis 94, and recesses 97 are formed in the opposing faces of the forceps members 61 and 91. Since this increases the creepage distance between the electrode part 63 of the first forceps member 61 and the electrode part 92 of the second forceps member 91, they can be more reliably insulated from each other.

While embodiments of the present invention have been described above, the technical range of the present invention is not limited to these embodiments, and various modifications can be made without departing from the spirit or scope of the present invention.

Figure 13:
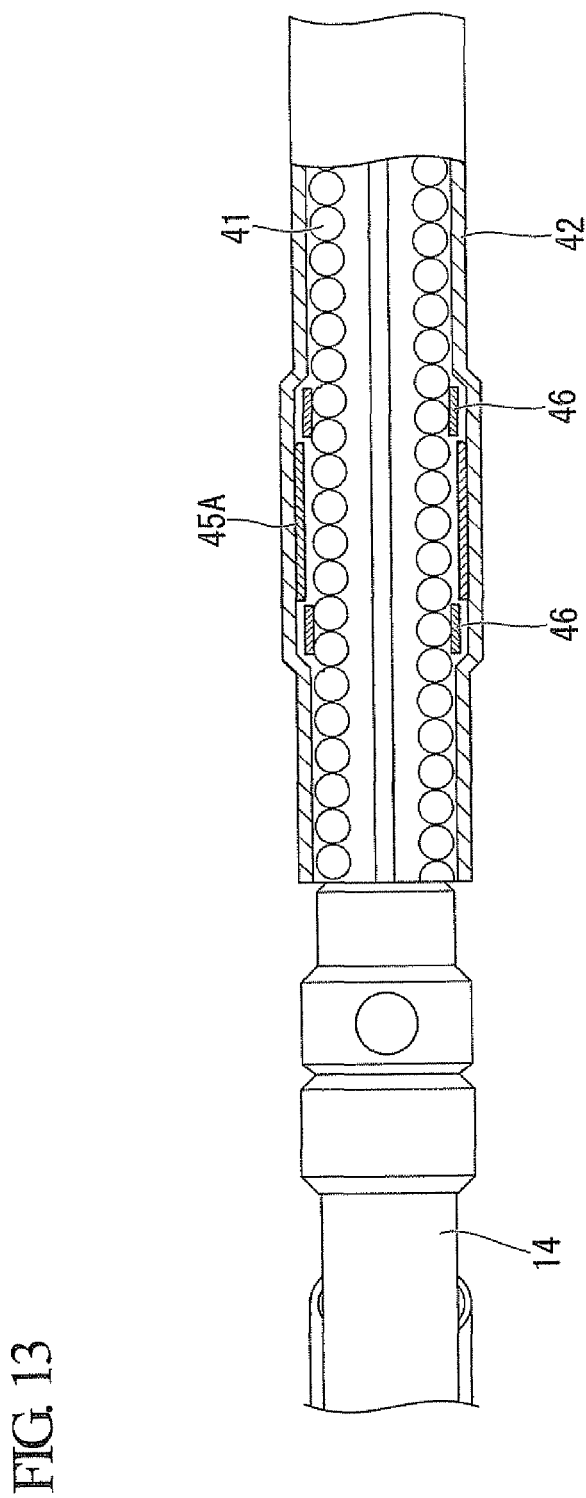
FIG. 13 is a cross-sectional diagram of one part of an insertion part in a treatment instrument for endoscope according to a modification of the present invention.

For example, in the examples described in the embodiments, the coil sheath 41 includes the small-diameter part 43, the ring member 45 is attached to the small-diameter part 43, so that the coil sheath 41 and the tube sheath 42 can rotate relative to each other but are unable to move relative to each other in the axial direction. This method has the advantage of enabling the coil sheath 41 and the tube sheath 42 to be assembled without increasing the diameter of the insertion part. In a modification shown in FIG. 13, instead of forming a small-diameter part on the coil sheath 41, a stopper ring 46, which has an outer diameter that is larger than the inner diameter of a ring member 45A pushed into the tube sheath 42, is attached by soldering or the like to the outer periphery of the coil sheath 41 so as to be positioned on each side of the axial direction of the ring member 45A.

In this configuration, the diameter of the part where the ring member 45A and the stopper 46 are attached is larger than when a small-diameter part is provided. However, in a treatment instrument or the like which has few restrictions on the size of its diameter, this is advantageous in that there is no need to cut the coil sheath 41, and the coil sheath 41 can be assembled to the tube sheath 42 more easily and with fewer processing steps.

In this case, it is possible to reverse the relationship between the sizes of the ring member 45A and the stopper ring 46, by pushing the stopper ring 46 into the tube sheath 42 and fixing the ring member 45A to the coil sheath 41.

Figure 14:
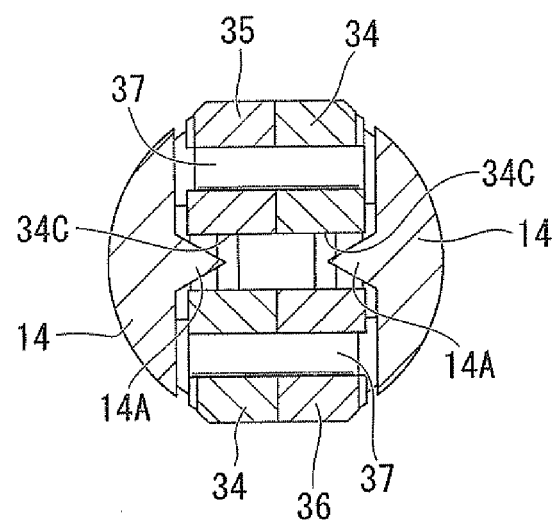
FIG. 14 is a cross-sectional diagram of a connection part in a treatment instrument for endoscope according to a modification of the present invention.

In the examples in the embodiments described above, a restriction wire is used to make a restriction part that restricts the axial rotation of a connection member. When the restriction wire is not being used as a power supply wire, alternatively, as in the modification shown in FIG. 14, it is possible to form a protrusion 14A protruding toward the connection member 34 on the cover 14; the protrusion 14A engages with the groove 34C in the connection member 34, thereby restricting the axial rotation of the connection member and the operation wire.

At this time, the protrusion 14A and the groove 34C can be provided on one side only.

The structures and configurations of the embodiments described above can be combined as appropriate.

While preferred embodiments of the present invention have been described above, these are not limitative of the invention. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A treatment instrument for endoscope comprising:
a first forceps member comprising a first electrode part, and a second forceps member;
a forceps rotation axis that supports the first forceps member and the second forceps member, such that the first forceps member and the second forceps member are capable of rotating about the forceps rotation axis relative to each other;
a first link member and a second link member;
a first link member rotation axis that supports the first forceps member and the first link member, and a second link member rotation axis that supports the second forceps member and the second link member, wherein the first link member and the second link member make the first forceps member and the second forceps member open and close;
a link support member supporting the first link member and the second link member in a state where the first link member and the second link member are separated at a predetermined interval at least when the first forceps member and the second forceps member are closed;
an operation part connecting to the link support member, the operation part opening and closing the first forceps member and the second forceps member by moving the first link member and the second link member; and
a first power supply wire, one end thereof being connected to the first electrode part by being attached to the forceps rotation axis, and another end thereof being connected to a current supply means providing a current to the first electrode part, the first power supply wire disposed in a separated space formed according to the predetermined interval between the first link member and the second link member by the link support member, wherein
a displacement of the first link member rotation axis and the second link member rotation axis toward the separated space is restricted by the first power supply wire.

2. The treatment instrument for endoscope according to claim 1, further comprising:

an operation member being provided with the link support member attached on a distal end thereof, the operation member being connected with the operation part;
a coil sheath into which the operation member is inserted; and
a tube sheath which the coil sheath is inserted into, and which is capable of rotating around an axis relative to the coil sheath, wherein
the relative movement of the coil sheath in the axial direction of the tube sheath is restricted by an advance/retraction restriction member attached in a lumen that is separated by more than a predetermined length from a distal end of the tube sheath; and
the coil sheath and the tube sheath maintain flexibility between the advance/retraction restriction member and the link support member.

3. The treatment instrument for endoscope according to claim 2, wherein the first power supply wire is disposed parallel to the operation member over a range from the one end to the another end.

4. The treatment instrument for endoscope according to claim 1, wherein the first link member and the second link member are parallel when the first forceps member and the second forceps member are closed.

5. The treatment instrument for endoscope according to claim 1, wherein:
the second forceps member has a second electrode part,
the first electrode part of the first forceps member and the second electrode part of the second forceps member are insulated from each other,
the first power supply wire and a second power supply wire are provided, one end of each power supply wire is connected with the first electrode part of the first forceps member and the second electrode part of the second forceps member, respectively, and
displacement of the first link member rotation axis and the second link member rotation axis toward the separated space are restricted by the first power supply wire and the second power supply wire.

* * * * *